US 6,806,260 B1

United States Patent
Hirofumi et al.

(10) Patent No.: US 6,806,260 B1
(45) Date of Patent: Oct. 19, 2004

(54) FUNCTIONAL CHITOSAN DERIVATIVE

(75) Inventors: Yura Hirofumi, Kawasaki (JP); Saito Yoshio, Yokohama (JP); Ishihara Masayuki, Tachikawa (JP); Ono Katsuaki, Tokorozawa (JP); Saeki Shiro, Funabashi (JP)

(73) Assignee: Netech, Inc., Kanagawa (JP)

( * ) Notice: Subject to any disclaimer, the term of this patent is extended or adjusted under 35 U.S.C. 154(b) by 0 days.

(21) Appl. No.: 09/831,419

(22) PCT Filed: Nov. 8, 1999

(86) PCT No.: PCT/JP99/06197

§ 371 (c)(1),
(2), (4) Date: Aug. 13, 2001

(87) PCT Pub. No.: WO00/27889

PCT Pub. Date: May 18, 2000

(30) Foreign Application Priority Data

Nov. 10, 1998 (JP) ............................................ 10-319209

(51) Int. Cl.[7] ..................... A61K 31/722; A01N 43/04; C08B 37/08; C07H 1/00
(52) U.S. Cl. ............................ 514/55; 536/20; 536/124
(58) Field of Search ............................. 514/55; 536/20, 536/124

(56) References Cited

U.S. PATENT DOCUMENTS 5,512,474 A * 4/1996 Clapper et al. ........ 435/240.243
5,747,475 A   5/1998 Nordquist et al. ............ 514/55

FOREIGN PATENT DOCUMENTS

| FR | 2 490 648 | | 9/1980 |
| JP | 10120705 | * | 7/1998 |
| JP | 10182332 A | * | 7/1998 |
| WO | WO 93/05793 | | 4/1993 |
| WO | WO 99/01498 | | 1/1999 |

OTHER PUBLICATIONS

Roberts G A F et al: "The Coupling of Chitosan to Preformed Polymer Beads"x Makromolekulare Chemie, Rapid Communications, Huthig und Wep Verlag. Basel, CH, vol. 10, No. 7, Jul. 1, 1989, pp. 339–343. XP000074704.
Patent Abstracts of Japan, vol. 1998, No. 10, Aug. 31, 1998 & JP 10 120705 A (Neetec:KK;Yaizu Suisan Kagaku Kogyo KK), May 12, 1998.
Patent Abstracts of Japan, vol. 1999, No. 05, May 31, 1999 & JP 11 043441 A (Ichimaru Pharcos Co Ltd; Yaizu Suisan Kagaku Kogyo KK; Neetec:KK), Feb. 16, 1999.
Sei–ichi Aiba et al. "Covalent immobilization of chitosan derivatives onto polymene film surfaces with the use of a photosensitive hetero–bifunctional crosslinking reagent". Biomaterials, Nov., 1987, vol. 8, pp. 481–488. XP–002062555.
Patent Abstracts of Japan, vol. 14, No. 188 (C–710), Apr. 17, 1990 & JP 02 032101 A (Kawaken Fine Chem Co Ltd). Feb. 1, 1990, abstract: examples 4–6; table 1.

* cited by examiner

Primary Examiner—James O. Wilson
Assistant Examiner—Everett White
(74) Attorney, Agent, or Firm—Pearne & Gordon LLP

(57) ABSTRACT

A functional chitosan derivative which comprises a chitin/chitosan, which is a natural polysaccharide, and incorporated therein at least one of a carbohydrate, a photo-reactive functional group, an amphipathic group, e.g. a polyoxyethylene alkyl ether, and a glycosaminoglycan and which, due to the incorporation, has solubility in a neutral medium, self-crosslinking ability, the property of highly containing water or healing wounds, and antithrombotic properties. Namely, the derivative has various properties required of health care materials such as medical products and cosmetics.

3 Claims, 7 Drawing Sheets

FUNCTIONAL CHITOSAN DERIVATIVE

TECHNICAL FIELD

The present invention relates to a novel functional chitin/chitosan derivative, and more specifically relates to a chitosan derivative with improved solubility, gel forming ability and hydrogel forming ability due to the incorporation of a carbohydrate having a reducing terminal and/or a photo-reactive functional group and/or an amphipathic group.

BACKGROUND ART

The application of natural materials has been widely researched in the medical and cosmetic fields for their biocompatibility such as their histocompatibilities and biodegradability. In particular, various uses can be conceived by solidification or formation of insoluble hydrogels by means of chelating with salts or crosslinking reactions.

For example, in recent years, research relating to the function of carbohydrate chains has become more active, making it clear that they play a considerable role in cell adhesion and viral infection. The carbohydrates in mammals exist mostly as composites such as glycoproteins and glycolipids, with some of these carbohydrate chains contributing to specific functional expressions. For this reason, these types of substances containing carbohydrate chain are often biologically active, but in practice, present problems in terms of their handling and cost.

On the other hand, in plants and marine organisms, carbohydrate chains exist as macromolecular substances for the skeletal structures of the organisms. Cellulose, pectin, gum arabic, polygalactomannan, arginic acid and the like are contained in plants and algae, and are macromolecular substances with high viscosity capable of being cheaply mass-collected. Additionally, chitin/chitosans are widely distributed in the exoskeletons of insects and the shells of crustaceans such as crabs and lobsters, glucosamin which is the constituent carbohydrate thereof having the function of an elicitor for protecting against infection and decomposition.

Since these carbohydrates exist as polysaccharides having extremely high molecular weights and also have high viscosity, their application to medicine such as in wound dressings, artificial skin, implants used in oral surgery or plastic surgery, hemostatics and adhesives, or to cosmetics such as humectants has been considered, but their range of application is limited due to the difficulty of chemically modifying them with regard to solubility in solvents and the like in comparison to proteinous ingredients.

Chitin/chitosans, which are unique even among polysaccharides, contain amino groups as constituent carbohydrate units, so that their use in conjunction with chemical crosslinking agents such as isocyanates, aldehydes and carbodiimides in wound dressings, anti-adhesion materials and decomposing absorbents has been studied.

However, chitins are not soluble in water due to their crystallinity, which is based on hydrogen bonds, and must be decomposed to low-molecular weight substances by means of hydrolysis or partially deacetylated in order to prepare them to be suitable for application to a wide range of industrial fields including medicine. Additionally, chitosans with increased carbohydrate units with amino groups exposed by active deacetylation for the purposes of improving the physical properties of chitins are soluble in acidic solvents including dilute organic acids, but are still extremely thick, making them difficult to handle in wound dressings and biological adhesion which are required to be easily worked on the scene of medical treatment. Additionally, since the thick chitosan solution does not retain a physiological pH, it is difficult to freely add physiologically active reagents used for therapeutic purposes, and there is the problem of toxicity when used with free chemical crosslinking agents, thus limiting the possibilities of use in the field of health care including medicine.

DISCLOSURE OF THE INVENTION

Upon performing diligent research, the present inventors found that the above-mentioned problems could be overcome by binding a carbohydrate having a reducing terminal and/or a photo-reactive functional group and/or an amphipathic group such as a polyoxyalkylene alkyl ether or the like and/or a glycosaminoglycan to at least a portion of the amino groups or hydroxyl groups in the glucosamin units forming the chitin/chitosans having structures with at least partially deacetylated poly-N-acetylglucosamin, thus achieving the present invention.

Thus, the present invention offers a functional chitosan derivative incorporating, in at least a portion of the 2-position amino groups in the glucosamin units forming an at least partially deacetylated chitin/chitosan, a carbohydrate having a reducing terminal as a first functionalization and/or a photo-reactive functional group as a second functionalization and/or an amphipathic group as a third functionalization and a glycosaminoglycan as a fourth functionalization. Here, the amphipathic group as the third functionalization may be incorporated into at least a portion of the hydroxyl groups at the 3- and 6-positions of the glucosamin units or acetylglucosamin units forming the chitin/chitosans. The functional chitosan derivative of the present invention changes the pH-dependent water solubility originally held by chitosan by incorporating carbohydrate chains having reducing terminal, making it soluble in water in the physiological pH region, enables the chitin/chitosans to become insoluble self-crosslinked bodies by incorporating photo-reactive functional groups, enables an advantageous gel forming ability and high water content to be achieved by incorporating the amphipathic groups and confers an anti-adhesion ability by incorporating the glycosaminoglycan.

By binding carbohydrates and/or photo-reactive crosslinking groups and/or amphipathic groups to chitin/chitosans which are known to have tissue compatibility and wound healing effects, the chitosan derivative of the present invention is given water solubility in the physiological pH region, self-crosslinking by means of covalent bonds (hardening) by means of a photoreaction or an insoluble gel forming ability based on intermolecular interactions, thus not only making it safely compatible with biological tissue in the physiological pH range, but also enabling the formation of a hydrogel having an arbitrary strength and water content. Furthermore, the hydrogel formed using the chitosan derivative of the present invention does not use free chemical crosslinking agents and is therefore safe, and is able to bind various physiologically active substances due to its high water content and water retention, having a wide range of uses as a healthcare material in the medical field as wound dressings, anti-adhesion materials, hemostatics, sealants for body fluids or gases, clathrates for drug delivery and encapsulating agents for cells, and also in the cosmetic field as protecting materials for the skin and hair.

BEST MODE FOR CARRYING OUT THE INVENTION

Figure 1:
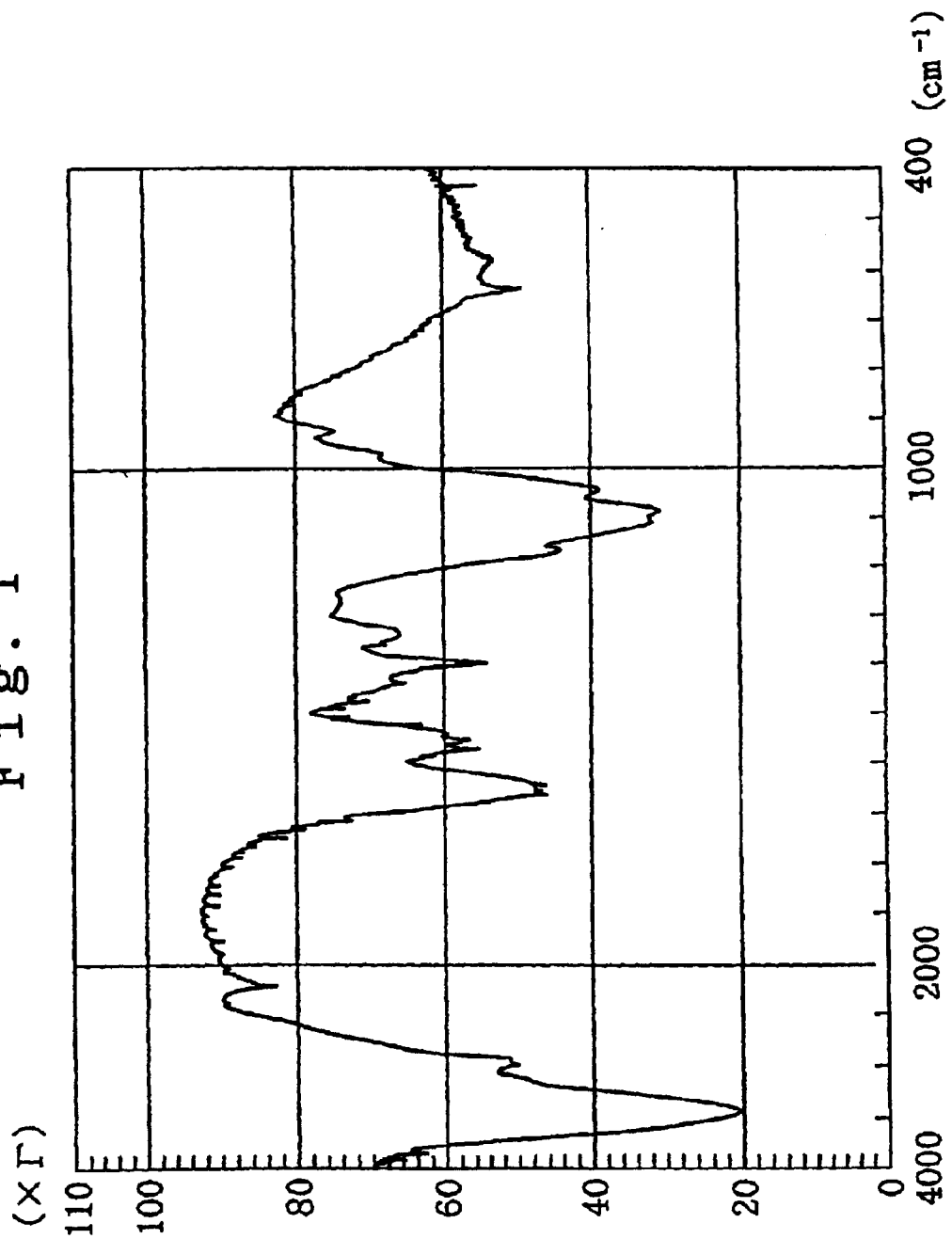
FIG. 1 is an IR spectrum of the compound 1-A1-a. Absorption due to the azide groups (—$N_3$) can be seen at 2250 $cm^{-1}$.
Figure 2:
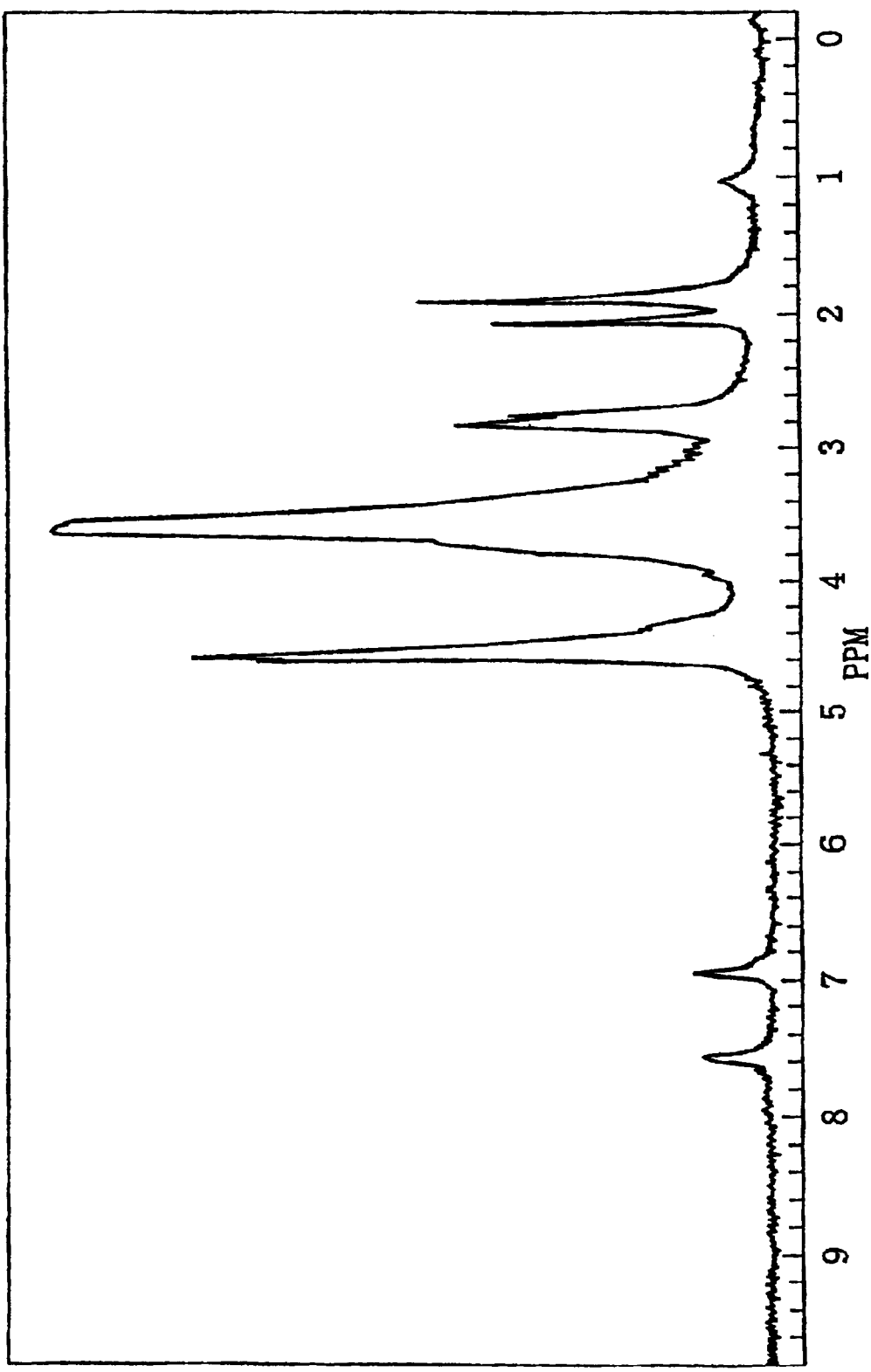
FIG. 2 is a ¹H-NMR spectrum of the compound a-A1-a. Peaks for the benzene rings can be seen at 7.2 and 7.6 ppm.
Figure 3:
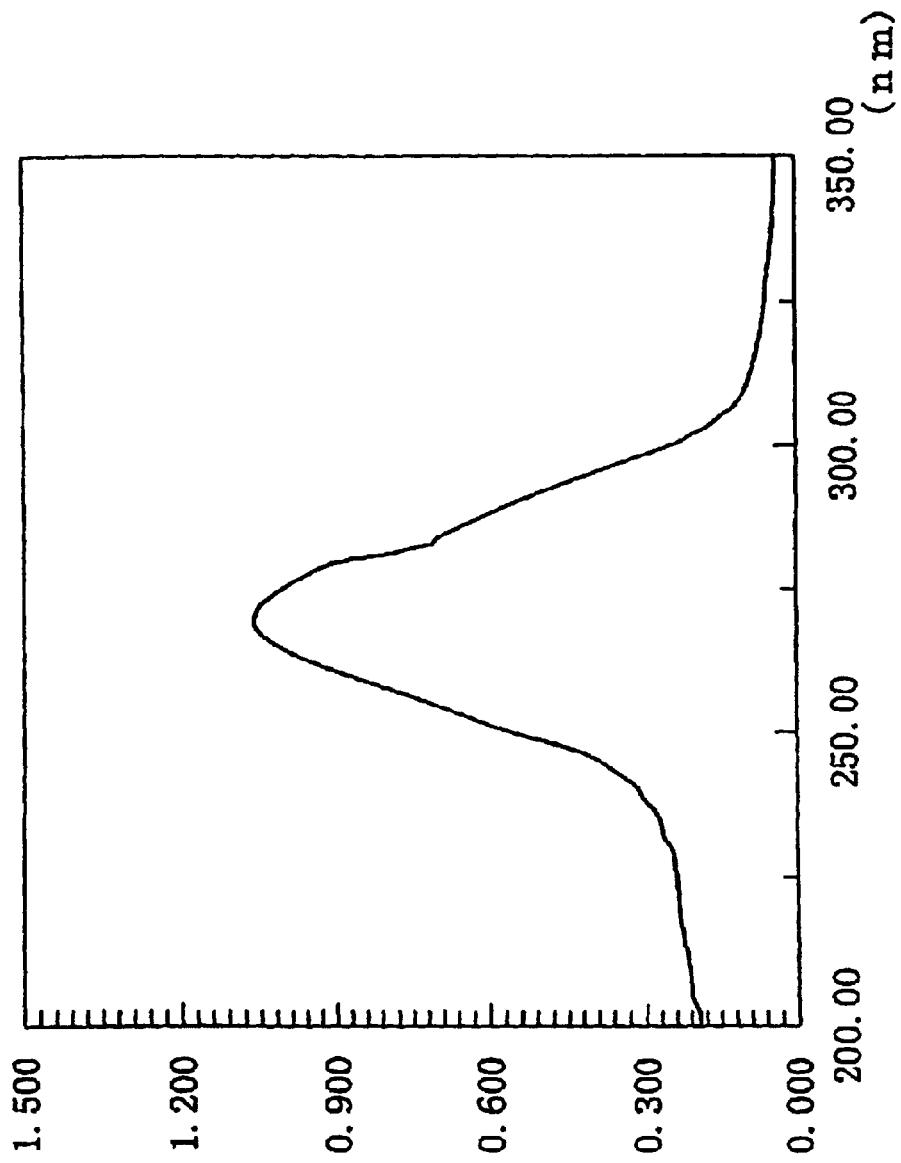
FIG. 3 is a UV spectrum of the compound 1-A1-a. A peak can be seen at 271 nm.
Figure 4:
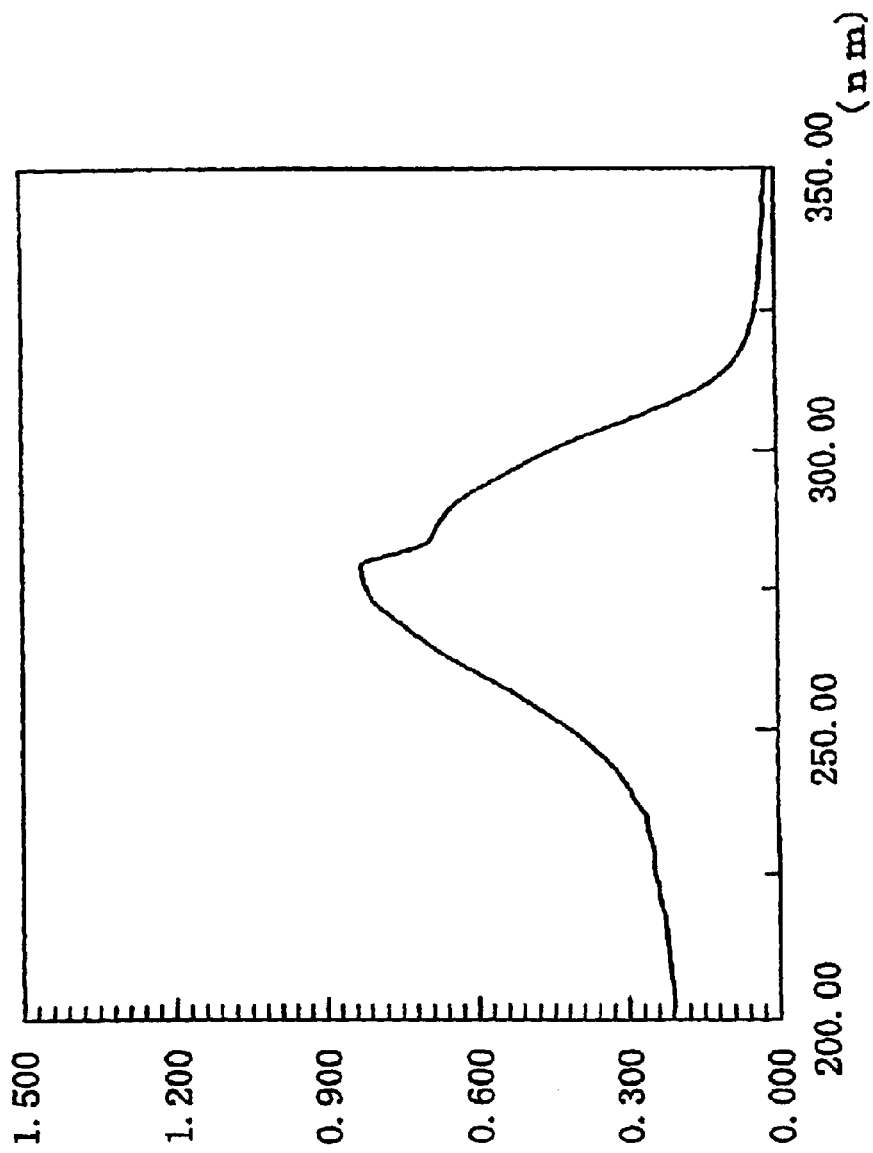
FIG. 4 is a UV spectrum of the compound 1-b. A peak can be seen at 278 nm.
Figure 5:
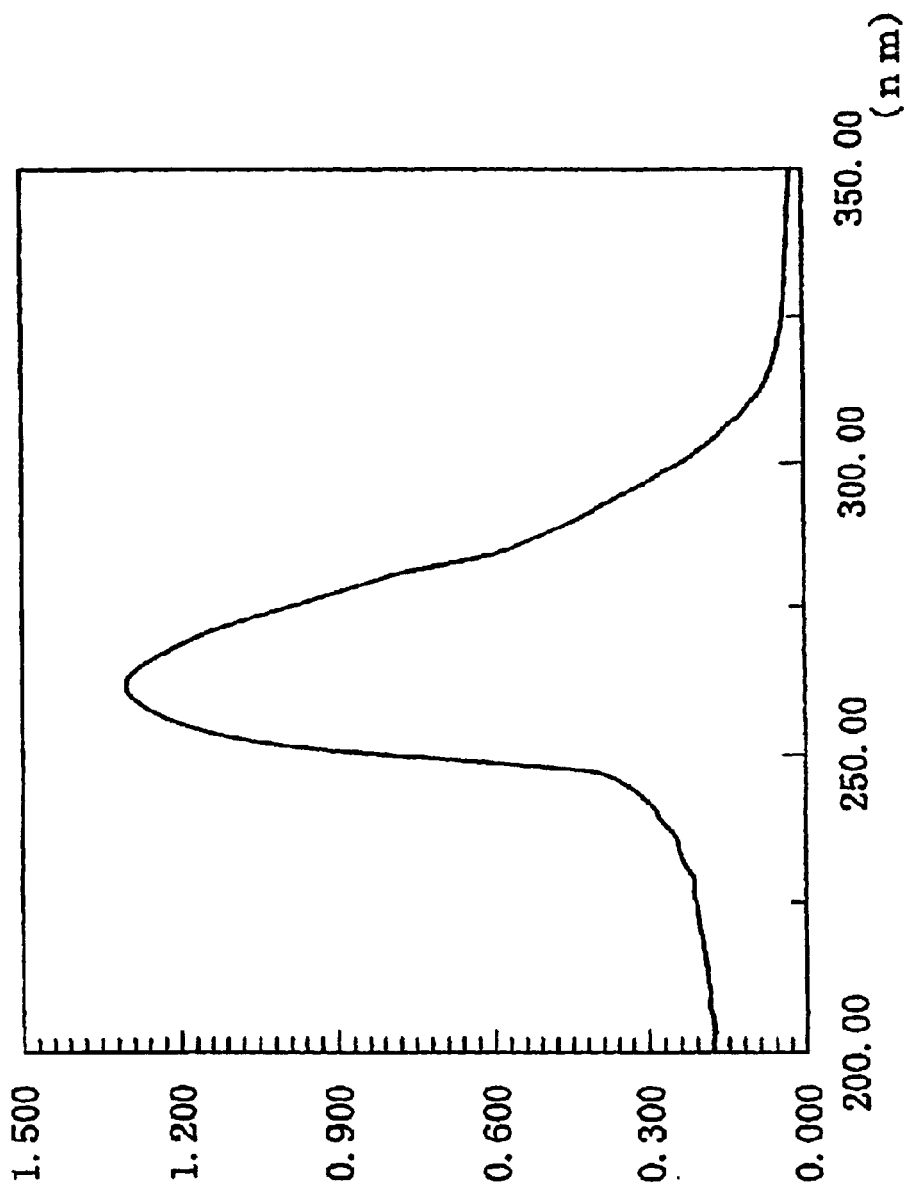
FIG. 5 is a UV spectrum of the compound 1-c. A peak can be seen at 262 nm.
Figure 6:
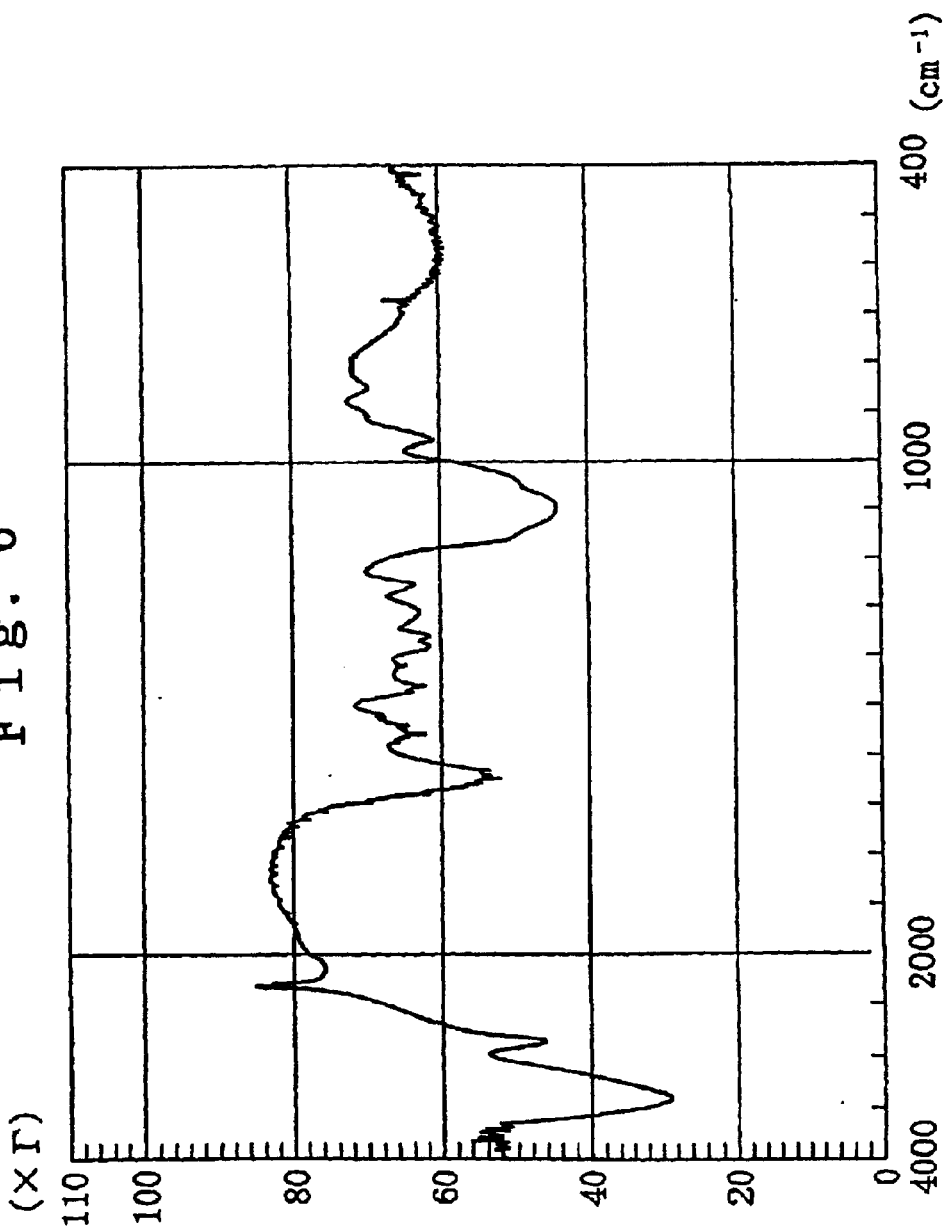
FIG. 6 is an IR spectrum of the compound 1-A1-I. Rocking absorption of the methylene group in the long chain alkyl groups can be observed at 840 cm¹.
Figure 7:
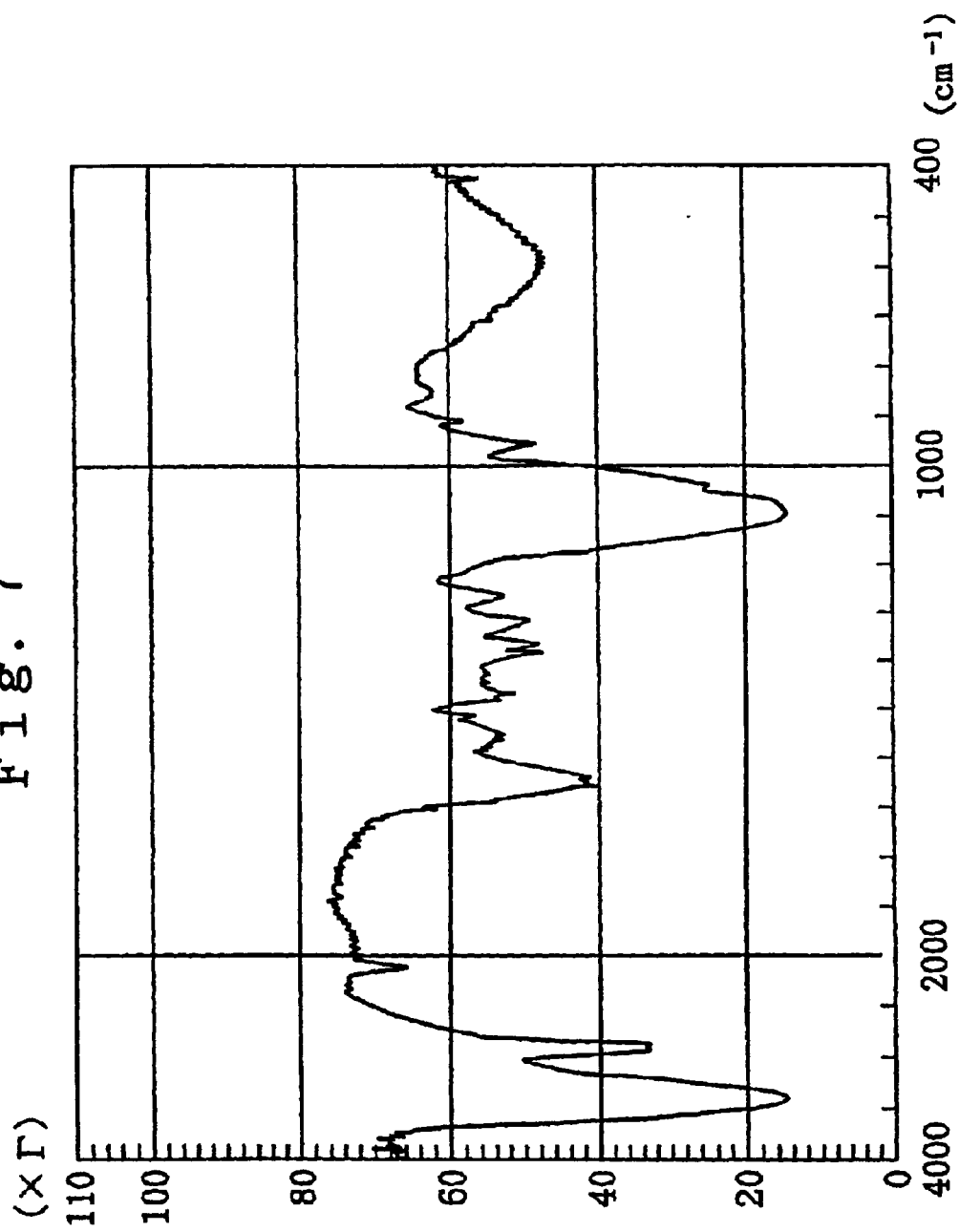
FIG. 7 is an IR spectrum of the compound 1-A1-a-I. Absorption by the azide groups can be observed at 2250 $cm^{-1}$, and rocking absorption of the methylene group of the long-chain alkyl groups can be observed at 840 $cm^{-1}$.

Herebelow, the functional chitosan derivative of the present invention shall be explained in further detail.

Normally, chitin/chitosans are deacetylated add-soluble fractions obtained by alkali processing chitin (poly-N-acetylglucosamins) originated from crab shells, and generally have the constituent units expressed by the following formulas (1) and (2) (wherein Q is $NHCOCH^3$).

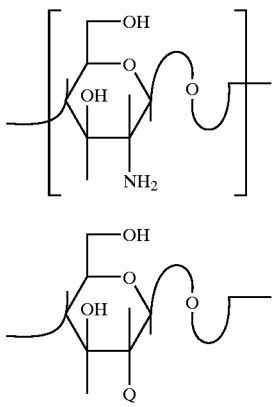

Among chitin/chitosans, some persons call those having a low degree of deacetylation (normally less than 40%) as "chitins" and those having a high degree of deacetylation (normally 40% or more) as "chitosans", but henceforth in the present specification, all chitin/chitosans which are at least partially deacetylated shall be referred to collectively as "chitosans". Additionally, in the present invention, chitosans are not limited to those of natural origin, and may be chemically modified carbohydrate chains having similar structures synthesized chemically or by genetic engineering.

Here, "degree of deacetylation" refers to the proportion of acetylamino groups in the 2-position of the carbohydrate units constituting the chitosan (or poly-N-acetylglucosamin), which have been converted to free amino groups by deacetylation. In the present specification, the degree of deacetylation is measured by means of the "colloidal titration method" described in "Health Foods Standard and Criterion (No. 4)", Japan Health Food and Nutrition Food Association (1996), p. 55.

The chitosan derivative of the present invention has been functionalized by further chemically modifying the chitosan, and the chitosan used as the raw material should preferably have a degree of deacetylation of at least 40%, preferably 60-100%, more preferably 65-95%. A chitosan having a 100% degree of deacetylation consists entirely of the constituent units of the above-given formula (1), and does not include the constituent units of formula (2).

Additionally, there are no particular restrictions on the molecular weight of the chitosan, and this can be changed of a wide range depending on the projected use of the chitosan derivative, but in general, the number-average molecular weight should be in the range of 5,000–2,000,000, preferably 10,000–1,800,000, more preferably 40,000–1,500,000.

The chitosan derivative of the present invention has a carbohydrate having a reducing terminal and or a photo-reactive functional group and or an amphipathic group incorporated into at least a portion of the amino group in the 2-position of the glucosamin unit of formula (1) and/or the hydroxyl group in the 3-position or 6-position of the acetyl-glucosamin unit of formula (2), and includes the constituent units indicated by the following formulas (1'), (2') and/or (3) (wherein R1 denotes a carbohydrate residual group having a reducing terminal or a photo-reactive functional group or an amphipathic group, R2 is a hydroxyl group or an amphipathic group, and Q is as defined above).

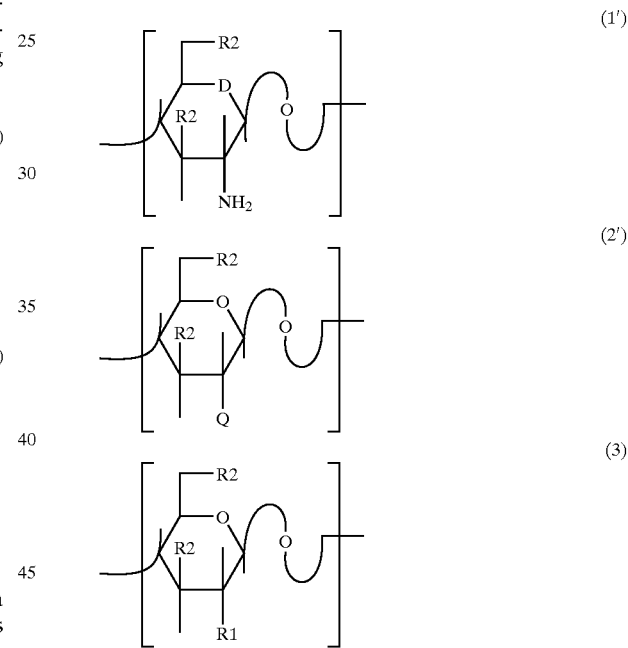

In other words, the chitosan derivative of the present invention incorporates at least one of a carbohydrate having a reducing terminal, a photo-reactive functional group, an amphipathic group or a glucosaminoglycan, and encompasses those composed of constituent units of the above formulas (1') and (2'), those composed of constituent units of (1') and (3), those composed of constituent units of (2') and (3), and those composed of constituent units of all (1'), (2') and (3). However, in the case where the chitosan derivative is composed only of constituent units of (1') and (2'), at least one of R2 is an amphipathic group. Additionally, there may be cases in which constituent units of formula (2') are not included depending on the degree of deacetylation of the chitosan used as the raw material, and there may be cases in which constituent units of formula (1') are not included depending on the degree of chemical modification. That is, the chitosan derivatives of the present invention encompass those composed only of constituent units of formula (3).

Additionally, the chitosan derivative of the present invention may contain in a single molecule, 2, 3 or 4 of any among the carbohydrate residual group having a reducing terminal, a photo-reactive functional group, an amphipathic group and a glycosaminoglycan.

According to the present invention, carbohydrates having reducing terminals used for chemical modification of the chitosan as a first functionalization include aldoses and ketoses, among which those having 20 or less constituent carbohydrate units, especially those with 1–7 units are preferably used. Specific examples include pentaoses and hexaoses such as glucose, fructose, galactose, fucose, mannose, arabinose, xylose, erythrose, hepturose and hexylose, amino carbohydrates such as glucosamin, N-acetylglucosamin and galacsamin; carbohydrate derivatives such as uronic acids and deoxysaccharides; di- and trisaccharides such as maltose, isomaltose, lactose, melibiose and maltotriose composed of carbohydrate chains combining the above-mentioned monosaccharides; and the various oligosaccharides, among which the neutral disaccharides such as maltose, lactose and melibiose are preferable.

While it is also possible to derive chitosans from organic compounds such as polyethers and polyhydric alcohols instead of the above-mentioned carbohydrates, It is preferable to use natural carbohydrate chains in consideration of biocompatibility.

The incorporation of the above-mentioned carbohydrates in the 2-position amino group of the glucosamin units of the chitosan of the above-given formula (1) can itself be performed using known methods. For example, methods of carboxylating the reducing terminal of a carbohydrate, then binding to the 2-position amino group by an amide bond (see, for example, Japanese Patent Application, First Publication No. H10-120705), or of aldehydating or carbonylating the reducing terminal of a carbohydrate, then binding to the 2-position amino group of a glucosamin unit by a reduction alkylation method by means of a Schiff base (see, for example, "Applications of Chitins and Chitosans", edited by Chitin/Chitosan Workshop, pp. 53–56, Feb. 20, 1990, published by Gihodo Shuppan KK).

The carbohydrate incorporated in the chitosan in the present invention is not limited to only one type, and it is possible to use a combination of 2 or more.

Specific examples of a carbohydrate side chain contained in R1 of the constituent unit of the above-given formula (3) constituting the chitosan derivative of the present invention include the following, but there is no restriction to these.

(i) Derived from lactose

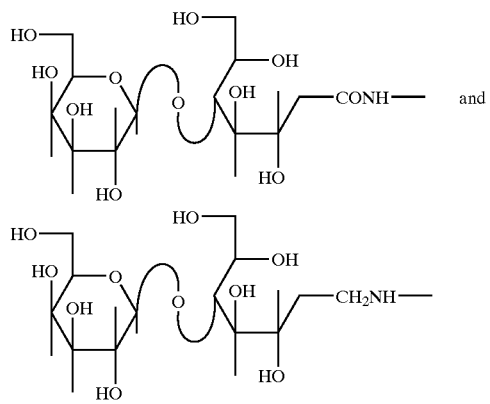

(ii) Derived from maltose

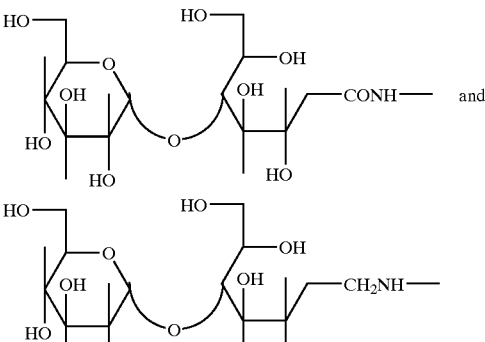

(iii) Derived from melibiose

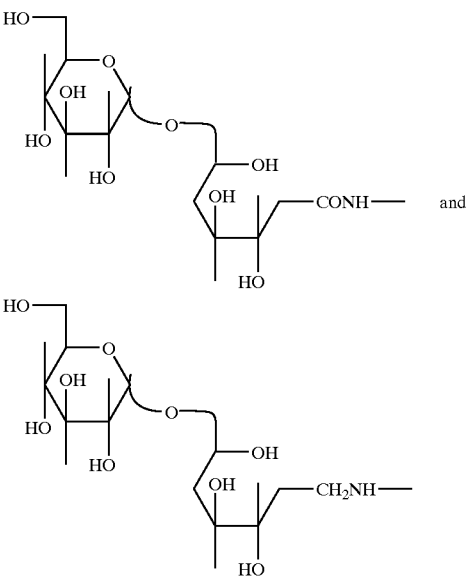

(vi) Derived from cellobiose

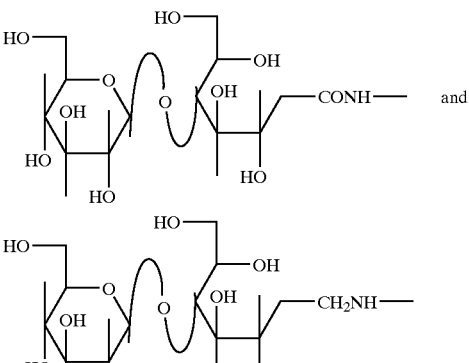

(v) Derived from laminaribiose

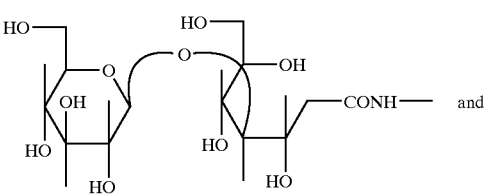

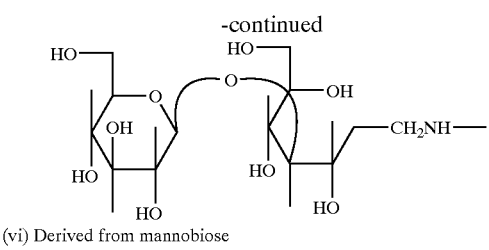

(vi) Derived from mannobiose

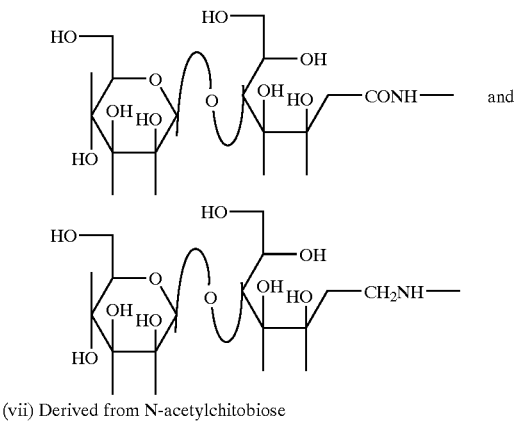

(vii) Derived from N-acetylchitobiose

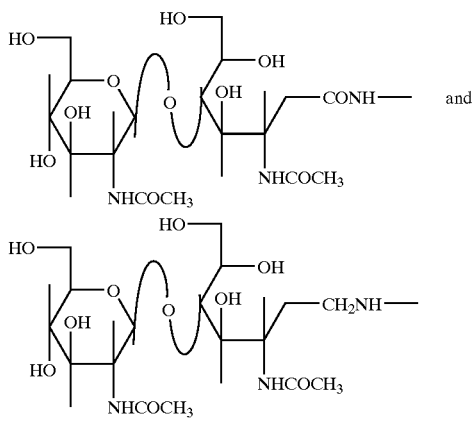

Of the carbohydrate side chains given in the above (i)–(vii), those on the left side represent residual groups incorporated by means of condensation between a carboxyl group on the carbohydrate and a 2-position amino group on the chitosan, while those on the right side represent residual groups bound by a Schiff base.

While the degree of substitution of 2-position amino groups in the glucosamin units of chitosan by carbohydrate side chains can be changed according to the physical properties desired in the final chitosan derivative, the degree of substitution should generally be in the range of 0.1–80%, preferably 0.5–60%, more preferably 1–40%. Here, the "degree of substitutions" of the carbohydrate side chain is the level to which the amino groups in the 2-position of the carbohydrate units constituting the chitosans are substituted by carbohydrate side chains, and denote the proportion of substituted amino groups with respect to the total number of free amino groups and substituted amino groups at the 2-position of the carbohydrate units constituting the chitosans. In the present specification, the degree of substitution of carbohydrate side chains is measured by the "phenol-sulfuric acid method" wherein the characteristic color emission due to a reaction between carbohydrate chains and phenol in sulfuric acid is sensed by light absorption at 490 nm (see J. E. Hodge, B. T. Hofreiter, "Methods in Carbohydrate Chemistry", ed. by R. L. Whistler, M. L. Wolfrom, vol. 1, p. 388, Academic Press, New York (1962)).

Additionally, the chitosan derivative of the present invention has as its second functionalization, self-crosslinking property by photo-irradiation due to incorporating photo-reactive functional groups in the 2-position amino groups in the glucosamin units of the above-given formula (1) constituting the chitosan.

The photo-reactive functional groups used for chemical modification of the chitosans according to the present invention are groups which react with each other and/or amino groups or hydroxyl groups present in the chitosan upon irradiation by ultraviolet light including the near-ultraviolet region of 200–380 nm to form crosslinking bonds including, for example, those derivable from cyclic unsaturated compounds such as benzophenones, cinnamic acids, azides, diolefins and bis-anthracene, especially preferable being those having carbonylazide groups, sulfonylazide groups and aromatic azide groups.

The incorporation of photo-reactive functional groups to the amino groups at the 2-position in the glucosamin units of the chitosans can itself be performed by known methods, for example, by a method of binding an azide compound having a carboxyl group to the 2-position amino group in the presence of a condensing agent (see Japanese Patent Application, First Publication No. H10-120705); or a method of reacting the azide compound with the 2-position amino group by means of an acid chloride group, an aldehyde group, an N-hydroxysuccinic acid imide ester group or an epoxy group (see "Applications of Chitins and Chitosans", edited by Chitin/Chitosan Workshop, pp. 53-5645-65, Feb. 20, 1990, published by Gihodo Shuppan KK).

In azide group crosslinking reactions, it has been conventionally held to be effective to use polyfunctional compounds such as bis-azides or above (see Japanese Patent Application, First Publication No. H9-103481), this is not necessary in the present invention, so that a chitosan derivative having adequate self-crosslinking ability can be obtained by incorporation of monoazide compounds.

Specific examples of a photo-reactive functional group R1 bound to the 2-position amino group in the constituent unit of the formula (3) forming the chitosan derivative of the present invention include, for example, those expressed by the following formulas (A) through (D). The group of formula (A) is derived from p-azidobenzoic acid, the group of formula (B) is derived from p-azidobenzaldehyde, the group of formula (C) is derived from p-benzoylbenzoic acid, and the group of formula (D) is derived from cinnamic acid.

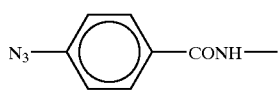

(A)

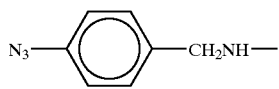

(B)

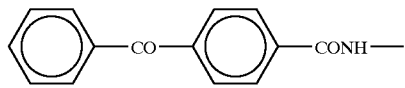

(C)

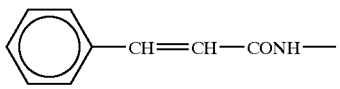
(D)

While the degree of substitution of these photo-reactive functional groups can be changed according to the degree of gelation (insolubility) due to the crosslinking reaction desired in the final chitosan derivative, but it is preferable for the degree of substitution of the photo-reactive functional groups to be within the range of 0.1–80%, preferably 0.5–50%, more preferably 1–30%. Here, the "degree of substitution" of the photo-reactive functional groups is the degree of substitution of the 2-position amino groups of the carbohydrate units forming the chitosans with photo-reactive functional groups, and is the proportion of substituted amino groups with respect to the total number of free amino groups and substituted amino groups at the 2-position of the carbohydrate units forming the chitosans. In the present specification, the degree of substitution of photo-reactive functional groups such as azide groups can be determined based on calibration curves obtained from characteristic absorption at 270 nm for 4-azidobenzoic acid.

The degree of substitution of the total of carbohydrate side chains and photo-reactive functional groups in the chitosan derivatives of the present invention is not particularly restricted, and may vary over a considerable range, but is usually in the range of 0.2–80%, preferably 1.5–65%, more preferably 3–50%.

Additionally, according to the present invention, an insoluble hydrogel with considerably improved water retention ability can be obtained by incorporating an amphipathic group to at least a portion of the 3- or 6-position hydroxyl groups in the carbohydrate units of formulas (1') and (2'), and the amino groups in the 2-position of the carbohydrate units of formula (3) constituting the chitosan. These amphipathic groups are groups having a hydrophobic block comprising a hydrophobic group and a hydrophilic block comprising a hydrophilic group, and often have a surfactant function. Among these those in which the molecular weight ratio between the hydrophobic blocks (X) and the hydrophilic blocks (Y) is X:Y=1:5 to 5:1 are preferably used, and non-ionic groups without dissociated ionic groups are more preferably used. In particular, those composed of a hydrophobic alkyl block and a hydrophilic polyocxyalkylene block and with a molecular weight of at least 90 are preferable, a polyoxyalkylene alkyl ether of 500–10,000 being more preferable. While a polyether not having a hydrophobic block may be used, a polyoxyalkylene alkyl ether is preferable for having both a hydrophobic block and a hydrophilic block in consideration of the improvement to the water retaining ability.

The incorporation of these amphipathic groups to the chitosan can be performed, for example, by a method of incorporating a compound having groups capable of reacting with amino groups to form covalent bonds, such as aldehyde groups or epoxy groups to a terminal portion of either the hydrophilic block or hydrophobic block of the amphipathic group, then reacting with the 2-position amino group of the glucosamin of the chitosan, a method of inducing a reaction between a polyoxyalkylene alkyl ether derivative having a carboxyl group with the chitosan in the presence of a condensing agent, or a method of inducing a reaction between a polyoxyalkylene alkyl ether derivative having an acid chloride group with a hydroxyl group or amino group in the chitosan.

For example, when incorporating a polyoxyalkylene alkyl ether group with an epoxy group on its terminal into an amino group in the chitosan, the amphipathic group R2 in the above-given formula (4) is expressed by the following formula (a), and when incorporating a polyoxyalkylene alkyl ether group with an aldehyde group on its terminal into an amino group of the chitosan, the amphipathic group R2 of the formula (4) is expressed by the following formula (b). Additionally, when binding a polyoxyalkylene alkyl ether group with an acid chloride group on its terminal to the 3- or 6-position hydroxyl group of the chitosan, the amphipathic groups R2' or R2" in the above formulas (1)–(4) are expressed by the following formula (c). In the below formulas (a)–(c), n and m are repeating units numbering 1 or more.

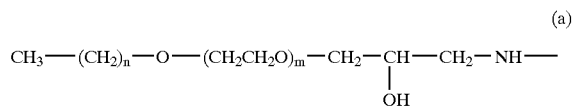

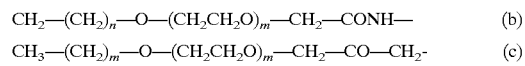

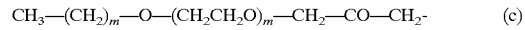

The degree of incorporation of amphipathic groups in the chitosan derivatives of the present invention is not particularly restricted, but should be within the range normally of 5–70%, preferably 15–55% based on the change in weight of the chitosan derivative after incorporation.

Furthermore, in the present invention, it is preferable to further add to the chitosan derivative having incorporated therein a carbohydrate side chain and a photo-reactive functional group, as a fourth functionalization, a function of promoting healing which is an additional function heavily desired in wound dressing, by incorporation of glycosaminoglycans.

The healing promotion effect, in addition to wound repair, optimizes turnover of keratinocytes in the skin-care area, thus contributing to prevention of wrinkles.

While it has been suggested that chitosans naturally have a healing promotion effect, there have been reports that further healing promotion can be expected by ionic complexation of the glycosaminoglycans which are naturally-occurring acidic mucopolysaccharides with the basic groups of the chitosan (see Krats et al., Sc and J Plat Reconstr Hand Surg, 31, 119–123 (1997)). That is, the cell growth factors for stimulating the proliferation of fibroblasts and smooth muscle cells, which occurs during the healing process, are activated by binding to sulfated carbohydrates in the glycosaminoglycans.

The incorporation of glycosaminoglycans to the chitosan of the present invention is not by the conventional ionic complexation method, and they are incorporated to the 2-position amino groups of the glucosamin unit of formula (1) by covalent bonds. The coupling method may, for example be the same method as the incorporation method for carbohydrates already explained, but in order to preserve sulfated carbohydrates to which cell growth factors can bind, it is possible to use a coupling method using aldehyde groups in which glycosaminoglycans are generated by means of periodic acid or nitrous acid decomposition.

Aside therefrom, coupling can be performed by binding through the above-mentioned chemical reaction to an insoluble self-crosslinked chitosan film due to photo-irradiation, or by binding by means of ionic complexation.

Specific examples of glycosaminoglycans incorporated in this way are those expressed by the following formulas, but there is no restriction to these.

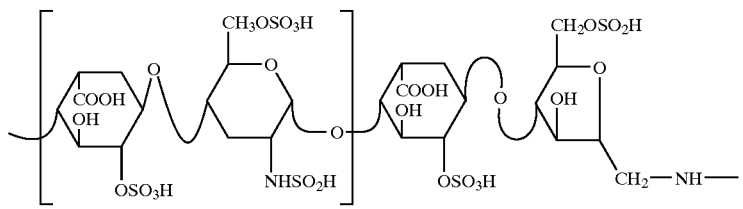

(Derived from Heparin)

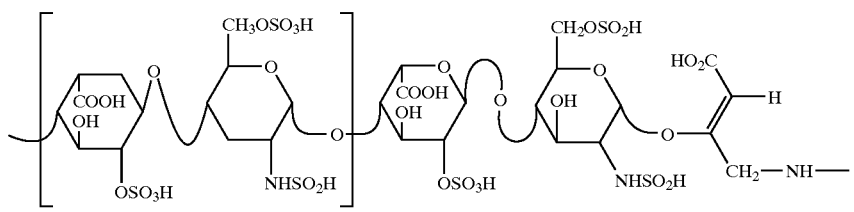

(Derived from Ileparin)

The degree of substitution of the glycosaminoglycans in the chitosan derivatives of the present invention is not particularly restricted, but should normally be within the range of 1–40, preferably 10–30%.

In the chitosan derivative of the present invention, at least one substituent group can be appropriately chosen for incorporation from among a carbohydrate having a reducing terminal (first function), a photo-reactive functional group (second function), an amphipathic group (third function) and a glycosaminoglycan (fourth function) according to the intended use.

For example, by providing both a photo-reactive functional group and an amphipathic group, it is possible to obtain a chitosan derivative, which forms a hydrogel having both greater strength and water retaining ability. A chitosan derivative such as this would be a novel functional material capable of forming a chitosan having a certain degree of wound healing, adhesion prevention, humectants and antibacterial effects into an insoluble gel with a desired strength in a short period of time, which could be widely applied in the field of health care such as in medicine and cosmetics. In particular, chitosan derivatives incorporating carbohydrates excel in solubility in the neutral region, so that they may be made into solutions in biological buffer solutions or cultures. Furthermore, chitosan derivatives having photo-reactive functional groups form thick aqueous solutions at a concentration of 0.1 wt % or more, and after application to tissue, can be made to form an insoluble gel which adheres firmly with the issue within a few minutes by irradiation by ultraviolet rays of a predetermined intensity. As a result, it can be freely coated on or implanted in burns, tissue deficient areas, surgical openings, cavities generated by losing teeth, bone deficient portions or the like, then irradiated for a short period of time to immediately form insoluble and adhesive hydrogel to shield off body fluids and gases. Additionally, the chitosan derivatives incorporating amphipathic groups and glycosaminoglycans, having a high water retention ability and healing promotion effect, can appropriately control the exudates from burns and skin ulcers and protect them against infection, thus reducing the hospitalization period and lightening the work load for medical staff.

Additionally since the freeze-dried flocculates of the chitosan derivative incorporating amphipathic groups such as polyoxyalkylene alkyl ethers have a water retention ability which is high enough to be capable of quickly absorbing nearly 100 times their own weight in water and forming insoluble gels, they can be used to absorb blood due to hemorrhaging from diseased organs or post-surgical bleeding, as well as inhibiting the activity of tumor cells by mean of intravascular hemostasis. The chitosan derivatives of the present invention having amphipathic groups, such as those being made to absorb an aqueous solution containing bioactive substances or drugs and allowed to form an insoluble gel, can be applied to drug delivery systems acting in a cite-specific manner which are not drug-releasable in the stomach but intestinally drug-releasable due to partial decomposition of the polyglucosamin skeletal structure by intestinal bacteria or enzymes.

When incorporating a photo-reactive functional group, the chitosan derivative of the present invention can be readily coated onto fiber products or resin sheets, then made insoluble by photo-irradiation, thus allowing for usage as an industrially inexpensive and functional surface reforming material. For example, by further incorporating a glycosaminoglycan, it is possible to make a gauze or bandage with an adhesion preventing function due to this type of processing, so that especially in the case of burns, the occurrence of secondary wounds during exchange of the wound protecting material can be effectively prevented.

Furthermore, the chitosan derivative of the present invention can be used in a wide range of applications in the health care field, such as by allowing for non- or less invasive procedures using catheters, or enabling cosmetics for the skin or hair which absorb ultraviolet rays or have a humectant effect.

Herebelow, the present invention shall be described in further detail by means of examples, but these are not such as to limit the scope of the present invention in any way.

EXAMPLE 1

Preparation of Chitosan Derivative

(1) Preparation of Chitosan Derivative Incorporating Carbohydrate Having Reducing Terminal (First Functionalization)

125 g of chitosan obtained by deacetylating chitin from crabs by an alkali process (degree of deacetylation 80%, molecular weight 1,000,000, produced by Yaizu Suisan Kagaku Industry Co., Ltd. (hereinafter referred to as "Compound 1")) were dispersed in 10 liters of a 50 mM aqueous solution of tetramethylethylenediamine (TEMED), after which 56.25 ml of hydrochloric acid were added and dissolved. 32.5 g of soluble carbodiimide (EDC) and 20.25 g of iodinated lactose were added to this chitosan solution, and the result was allowed to react for 24 hours at room temperature. Unreacted substances of a molecular weight of 10,000 and below in the reaction solution were removed by ultrafiltration, to obtain a chitosan derivative wherein the 2-position amino group in the glucosamin units forming the chitosan were substituted with lactose (hereinafter referred to as "Compound 1-A1"; degree of lactose substitution 2%). Additionally, using the same method as above aside from making the amounts of iodinated lactose and EDC respectively 607.5 g and 997.7 g, another lactose-substituted chitosan derivative (hereinafter referred to as "Compound 1-A2"; degree of lactose substitution 40% ) was obtained.

A maltose-substituted chitosan derivative was obtained by the same method as described above aside from replacing the 20.25 g of iodinated lactose with 20.25 g of maltose (hereinafter referred to as "Compound 1-B1"; degree of lactose substitution 0.5%). Additionally, the amounts of the iodinated maltose and EDC were changed respectively to 620.0 g and 978.0 g to obtain another maltose-substituted chitosan derivative (hereinafter referred to as "Compound 1-B2"; degree of maltose substitution 24%).

A melibiose-substituted chitosan derivative was obtained by the same method as described above, except that the 20.25 g of iodinated lactose were replaced with 20.0 g of melibiose (hereinafter referred to as "Compound 1-C1"; degree of lactose substitution 0.5%). Additionally, using the same method as above aside from making the amounts of iodinated melibiose and EDC respectively 620.0 g and 978.0 g, another lactose-substituted chitosan derivative (hereinafter referred to as "Compound 1-C2"; degree of melibiose substitution 37%) was obtained.

(2) Preparation of Chitosan Derivative Incorporating Photo-reactive Functional Group (Second Functionalization)

1 g of the chitosan (Compound 1) used in Example 1 (1) was dissolved in 100 ml of a 50 mM aqueous TEMED solution. 0.7 g of EDC and 0.2 g of p-azidobenzoic acid were added to this chitosan solution, then allowed to react for 72 hours. Unreacted substances of a molecular weight of 1000 and below in the reaction solution were removed by ultrafiltration, to obtain a chitosan derivative wherein the 2-position amino group in the glucosamin units forming the chitosan were substituted with azide compounds (hereinafter referred to as "Compound 1-a"; degree of p-azidobenzoic acid substitution 2.5%). 0.7 g of water-soluble carbodiimide (EDC), 0.27 g of parabenzoylbenzoic acid or 0.09 g of cinnamic acid were added to a solution obtained by dissolving 1 g of the chitosan (Compound 1) into 100 ml of a 50 mM aqueous TEMED solution, and allowed to react for 72 hours. Unreacted substances of a molecular weight of 10,000 and below in the reaction solution were removed by ultrafiltration, to obtain chitosan derivatives incorporating parabenzoylbenzoic acid and cinnamic acid as photo-reactive functional groups (hereinafter referred to as "Compound 1-b"(degree of substitution 1.3%) and "Compound 1-c"(degree of substitution 0.5%)).

Next, 1 g each of the Compound 1-A1 (2% lactose-substituted chitosan derivative) and Compound 1-B1 (0.5% maltose-substituted chitosan derivative) prepared in Example 1(1) were separately dissolved in 100 ml of a 50 mM aqueous TEMED solution. 0.35 g of EDC and 0.2 g of azidobenzoic acid were added to each chitosan derivative solution, and allowed to react for 72 hours. Unreacted substances of a molecular weight of 10,000 and below in the reaction solution were removed by ultrafiltration, to obtain chitosan derivatives incorporating carbohydrates and photo-reactive functional groups (first and second functionalizations) (hereinafter referred to respectively as "Compound 1-A1-a" and "Compound 1-B1-a"; degree of substitution by azidobenzoic acid, both 2.5%).

(3) Preparation of Chitosan Derivative Incorporating Amphipathic groups (Third Functionalization)

1 g of a hydrochloride of the chitosan (Compound 1) used in Example 1 was dissolved in 40 ml of purified water, and 7.76 g of lauryl alcohol polyethylene glycol (15 repeating units) glycydyl ether (EX-171; Nagase Kasei Kogyo). After allowing to react for 24 hours at 30 degrees, methanol was added in excess to reprecipitate the chitosan ingredients. After dialysis, the result was freeze-dried to obtain a chitosan derivative incorporating an amphipathic group (hereinafter referred to as "Compound 1-I").

In the same manner as described above aside from using the compound 1-A1 (lactose-substituted chitosan derivative) prepared in Example 1(1) instead of the chitosan (Compound 1), a chitosan derivative with a carbohydrate and an amphipathic group (first and third functionalizations) was obtained (hereinafter referred to as "Compound 1-A1-I").

In the same manner as described above aside from using the compound 1-a (azidobenzoic acid-substituted chitosan derivative) prepared in Example 1(2) instead of the chitosan (Compound 1), a chitosan derivative with a photo-reactive functional group and an amphipathic group (second and third functionalizations) was obtained (hereinafter referred to as "Compound 1-a-I").

In the same manner as described above aside from using the compound 1-A1-a (lactose- and azidobenzoic acid-substituted chitosan derivative) prepared in Example 1(2) instead of the chitosan (Compound 1), a chitosan derivative with a carbohydrate and an amphipathic group (first, second and third functionalizations) was obtained (hereinafter. referred to as "Compound 1-A1-a-I").

EXAMPLE 2 pH Solubility of Chitosan Derivative

The ranges of solubility of the 0.1% aqueous solution of the carbohydrate-substituted chitosan derivatives prepared in Example 1(1) are shown in the following Table 1.

TABLE 1

Soluble pH Region

| Compound | pH Region |
|---|---|
| 1 | pH 4.0 or less |
| 1-A1 | pH 7.5 or less |
| 1-A2 | pH 13.0 or less |
| 1-B1 | pH 6.8 or less |
| 1-B2 | pH 13.0 or less |
| 1-C1 | pH 6.8 or less |
| 1-A2 | pH 13.0 or less |

As shown in the above Table 1, the incorporation of disaccharides into the chitosan moderates the acid-dependent water solubility of the chitosan indicated by the untreated chitosan (Compound 1), thus allowing for solubility in the neutral region.

EXAMPLE 3

Evaluation of Ability to Form Insoluble Self-crosslinked Structures

Respectively 10 μg of the Compound 1-A (azidobenzoic acid-substituted chitosan derivative) prepared in Example 1(2), and Compounds 1-A1-a and 1-B1-a (lactose- or maltose-, and azidobenzoic acid-substituted chitosan derivatives) were dissolved in distilled water to form 1 wt % aqueous solutions, which were then placed on a glass plate. Immediately thereafter, they were irradiated with ultraviolet rays (200–380 nm, 5.5 mW/cm$^2$) for 10–90 seconds. Then, the insolubilized chitosan derivative gel was immersed in 100 ml of distilled water for 24 hours, to dissolve out the water-soluble chitosans, and the result dried.

The change in weight prior to and after ultraviolet irradiation was measured, and gelation rate was determined. The results are shown in the following Table 2.

TABLE 2

Insoluble Gelation Rate of Photo-hardened Chitosan

| | Weight Remaining After Water-Rinsing/ Original Weight | | |
|---|---|---|---|
| Irradiation Time | 1-a | 1-A1-a | 1-B1-a |
| 10 seconds | 0.61 | 0.61 | 0.58 |
| 30 seconds | 1.01 | 0.99 | 1.01 |
| 60 seconds | 1.00 | 1.00 | 0.98 |
| 90 seconds | 0.99 | 0.99 | 1.00 |

As shown in Table 2, the chitosan derivative of the present invention having photo-reactive functional groups (second functionalization) was almost completely crosslinked by ultraviolet irradiation at an extremely short time of 30 seconds to form a water-insoluble chitosan hydrogel. Additionally, since the chitosan derivative incorporating a carbohydrate (first and second functionalizations) is soluble in the neutral region, a solution was able to be formulated at a physiological pH. These first and second functionalized chitosan derivatives exhibited formation of an insoluble gel, i.e. self-crosslinking, under the same conditions without depending on the type of disaccharide incorporated. Furthermore, from this self-structuring property, it is clear that the insoluble gel formation time can be shortened to 1 second or less by using stronger ultraviolet radiation.

EXAMPLE 4

Evaluation of Strength of Water-insoluble Hydrogel

Using the chitosan derivative 1-a with the second functionalization and the chitosan derivative 1-A1-a with the first and second functionalizations, 1, 3 and 5 wt % aqueous solutions were prepared. Next, two 2 mm thick slices of ham cut into 2×3 cm portions were laid out to form a piece of 2×6 cm, and the above-described solutions were applied to a thickness of 2 mm in an area of 2×2 cm centered at the boundary between the two slices.

Immediately thereafter, the applied 1-a and 1-A1-a were irradiated with ultraviolet rays for 30 seconds to stick the two slices of ham together. One of the two slices of ham was anchored to a stand by means of a grip, and a gradually increasing weight was applied to the end of the other piece of ham, to measure the weight at which 1-a and 1-A1-a were ripped apart.

As a comparative example, the same process was performed using a commercially available fibrin glue (Veriplast, product of Hoechst Marion Roussel).

Additionally, ham was affixed to and sealed against one end of a tube having a diameter of 6 mm, a cut of 6 mm was made, and a seal of 2 mm of 1-a or 1-A1-a was applied, then irradiated with ultraviolet rays. Air was fed from the other end of the tube, and the pressure at which the air began to leak from the cut was measured.

The weight per sectional area when the gel broke in the former experiment and the pressure at which the air began to leak in the latter experiment are shown in the following Table 3. Here, the weight and pressure in Table 3 are defined as follows.

* Weight: The weight (10$^2$ kg/m$^2$) per unit of sectional area on the gel when the gel joining the ham broke.
** Pressure: The pressure (Pa) per unit area when the compressed air caused air to begin leaking from the gel covering the cut in the ham.

TABLE 3

| | Strength of Hydrogel | | | | | |
|---|---|---|---|---|---|---|
| Material | 1-a | | 1-A1-a | | Veriplast | |
| Concentration | Weight | Pressure | Weight | Pressure | Weight | Pressure |
| 1% | 1.8 | 3.2 | 1.4 | 4.7 | 4.0 | — |
| 3% | 3.1 | 3.7 | 2.8 | 3.7 | (conc. | (conc. |
| 5% | 4.2 | 4.6 | 4.3 | 4.3 | 4%) | 4%) |

As is clear from the results shown in the above Table 3, the chitosan derivatives incorporating azide compounds formed an extremely strong water-insoluble chitosan hydrogel with ultraviolet radiation of only a short time. At this time, peeling of the chitosan gel from the ham was not observed under any conditions. In contrast, the veriplast used as a control exhibited severance accompanied by peeling from the ham. 1-A1-a with the first functionalization was able to be prepared into an aqueous solution in the neutral region.

Additionally, the strength of the insoluble chitosan gel was able to be easily controlled by the concentration of the aqueous solution prior to hardening. This strength was roughly the same as the commercially available fibrin glue.

EXAMPLE 5

Evaluation of Hair Protection Function

A1:1:1 mixture (hereinafter referred to as "1-abc") of the chitosan derivatives 1-a (azidobenzoic acid), 1-b (parabenzoylbenzoic acid) and 1-c (cinnamic acid) having photo-reactive functional groups prepared in Example 1(2)

was made. 0.25 g of human hair were washed with a commercially available shampoo and rinsed with distilled water. After drying, it was left for 1 hour at a humidity of 95% and 37° C., then immersed for 10 minutes in a 0.1 wt % aqueous solution of 1-abc. The treated hair was opened out onto filter paper to absorb the excess aqueous solution, then irradiated with ultraviolet rays for 5 minutes. Then, hair irradiated with ultraviolet rays was immersed and rinsed in distilled water for 30 minutes, after which the hair weight prior to and after the 1-abc treatment were measured and compared. As a control, the same evaluation was made on untreated chitosan (Compound 1) and 1-A1 incorporating only lactose. The results are shown in Table 4.

TABLE 4

| Hair Treating Compound | Increased Weight Per Gram of Hair |
|---|---|
| 1 | 0.09 g |
| 1-A1 | 0.11 g |
| 1-abc | 0.15 g |

As shown in the above Table 4, the chitosan derivative of the present invention incorporating photo-reactive functional groups was effectively insolubilized and anchored to the hair surface by means of ultraviolet absorption, thus achieving high water retaining ability. This suggests that the chitosan derivative of the present invention has water retaining and ultraviolet ray shielding effects, thus maintaining a long-term coating and conferring gloss to hair. In contrast, the chitosan derivative 1-A1 incorporating only a carbohydrate is soluble in water, so that no meaningful results were seen in comparison to the untreated chitosan 1.

EXAMPLE 6

Evaluation of Hemostasis Effect 1, 3 and 5 wt % aqueous solutions of the chitosan derivative 1-a incorporating a photo-reactive group (azidobenzoic acid), and the chitosan derivative 1-A1-a further incorporating a carbohydrate (lactose) were prepared. A Wistar rat (female, 4 weeks old) was ventrotomized under pentobarbital, and a cut 2 mm deep and 2 mm long was made in each lobe of the lung. The portal vein was immediately clipped, the blood wiped off, and the prepared aqueous solution was applied. After ultraviolet irradiation for 30 seconds with a pin-point type ultraviolet radiation device (SpotCure, Ushio Electric), the clip was removed and the blood flow allowed to resume. This series of hemostatic procedures was completed within 1 minute. As a result, a good insoluble gel was formed by ultraviolet irradiation with chitosan solutions of each concentration, completely stanching blood flow from the cut surface.

Next, a cannula was inserted from the portal vein, and PBS with 0.5 mM of EDTA added thereto was injected by a peristalic pump. The blood in the liver was immediately replaced with PBS by severing the subabdominal vein. At this time, the liver turns a tan color due to the replacement with PBS, but PBS replacement does not occur at the portions in which there are obstacles to blood flow and the blood is congested, and the characteristic reddish brown color is maintained there.

In the present test, some reddish blood congestion was observed in the parts where the blood was stopped at the cut by means of the chitosan derivative of the present invention, but overall, blood replacement similar to the other liver tissue in which a cut was not made was observed.

EXAMPLE 7

Evaluation of Cell Response 0.1 wt % aqueous solutions respectively of the chitosan derivative 1-a with the second functionalization, and the chitosan derivatives 1-A1-a and 1-B1-a with the first and second functionalizations were prepared. 1 ml of the chitosan derivative solutions prepared in polystyrene culture dishes having a diameter of 35 mm, then let stand for two hours. Thereafter, the solution was disposed of and the result was irradiated with ultraviolet rays for 5 minutes, then rinsed three times with PBS.

As a control, a culture dish adsorbed and coated using fibronectin (F) and gelatin (G) of 0.025 wt % was used. Additionally an untreated culture dish (N) was also prepared.

These culture dishes were seeded with $10^6$ human vascular endothelial cells (VEC) from the human umbilical cord, fibroblasts (FIB) from neonatal skin, smooth muscle cells (SMC) from the coronary artery of rats and neonatal keratinocytes (KER) (all from Chronetics), and these were cultured for 8 hours at 37° C. The cell adsorption rate at this time is shown in Table 5.

TABLE 5

| Proportion of Seeded Cells Adsorbed to the Culture Dish (%) | | | | |
|---|---|---|---|---|
| Treating Substance | VEC | FIB | SMC | KER |
| N (untreated) | 10 | 23 | 21 | 26 |
| F (fibronectin) | 47 | 48 | 47 | 48 |
| G (gelatin) | 46 | 44 | 47 | 48 |
| 1-a | 8 | 10 | 11 | 34 |
| 1-A1-a | 8 | 5 | 7 | 31 |
| 1-B1-a | 8 | 4 | 21 | 37 |

As shown in Table 5, while the endothelial cells such as vascular endothelial cells, fibroblasts and smooth muscle cells exhibited a tendency toward extremely suppressed adhesion with respect to the chitosan derivatives of the present invention, the epithelial keratinocytes exhibited a tendency toward adhesion similar to fibronectin and gelatin which are known cell-adhesion proteins. The highest cell adhesion suppression tendency was observed in the chitosan derivative 1-A1-a incorporating lactose.

Furthermore, a cylindrical partition wall having a diameter of 15 mm was provided at the center of the culture dish, with the outside of the partition wall being treated with fibronectin, and the inside being treated with chitosan derivatives 1-a, 1-A1-a and 1-B1-a. After seeding the outside fibronectin phase with the above-described cells and adhering the cells, the partition wall was removed and a long-term culture was performed, upon which aside from the keratinocytes, none of the cells had transferred to the chitosan derivative treated phase inside the partition wall, and no cell growth could be observed even after two weeks. At this time, the cell survival rate was extremely good in all of the culture dishes.

The above results suggest the possibility that after being insolubility-treated at a wounded portion, the chitosan derivative of the present invention will obstruct the intrusion of granulation tissue generated in the treatment process, thereby effectively inhibiting adhesion. This type of hardening is expected to contribute considerably to the safe exchange of dressings on wounds, especially burns, and after a stent treatment for preventing reclosure of the coronary artery, prevention of reclosure due to proliferation of smooth muscle cells and the like.

Additionally, in the dermal region, it achieves adhesion and free movement of epithelial keratinocytes, and can therefore be expected to boost skin regeneration and have a skin beautifying effect by smoothing wrinkles. On the other hand, the photo-reactive functional groups such as azide groups, benzophenone groups and cinnamic acid capable of being incorporated by the present invention absorb and react with ultraviolet rays, and can therefore be expected to be capable of being used as a raw material for cosmetic products having a whitening effect due to shielding of ultraviolet rays.

EXAMPLE 8

Evaluation of Water Retention Rate

The following experiments were performed using the chitosan derivative 1-I incorporating only an amphipathic group (third functionalization) prepared in Example 1(3), the chitosan derivative 1-A1-I incorporating only the first and third functionalizations, the chitosan derivative 1-a-I incorporating the second and third functionalizations, the chitosan derivative 1-A1-a-I incorporating the first, second and third functionalizations, and for comparison, the untreated chitosan (compound 1) and a derivative (1-A1) incorporating only a carbohydrate.

These were freeze-dried, then 1 g of the freeze-dried flocculate was put into a flask having a capacity of 100 cc, and 100 ml of distilled water were added. After 5 hours, the moisture was absorbed to form a gelatinous transparent gel, and after disposing of the moisture, which was left without being absorbed, the weight of the gelatinous gel was measured. The results are shown in the following Table 6.

TABLE 6

Water Absorption Weight (g) of Chitosan Derivative

| Material | Weight |
| --- | --- |
| Chitosan (untreated) | Unmeasurable due to complete dissolution after 5 hours |
| 1-A1 (lactose) | Unmeasurable due to complete dissolution after 5 hours |
| 1-I | 72 |
| 1-A1-I | 75 |
| 1-a-I | 70 |
| 1-A1-a-I | 68 |

As shown in Table 6, the chitosan derivative of the present invention incorporating an amphipathic group (polyoxyalkylene alkyl ether group) clearly has a high water-retaining ability, such as to be able to absorb approximately 70 times its own weight of water. Additionally, the hydrogelation was completed within 10 second, but maintained its gel form even 5 hours after measurement. Additionally, the compound 1-a-I having a photo-reactive functional group and an amphipathic group became a gel with even higher strength due to ultraviolet irradiation.

EXAMPLE 9

Blood Solidification Test 0.1 g of freeze-dried flocculates of the chitosan derivatives 1-I and 1-a-I obtained by the present invention were added to 3 ml of fresh human blood collected with the addition of citrate-phosphate-dextrose (CPD). 1-I and 1-a-I immediately absorbed the water content in the blood to form an insoluble hydrogel, and when (I)-1-A was irradiated with ultraviolet rays, the adhesion between the tissue surface and gel increased. These high-water-retention chitosan derivatives swell with water when injected into blood vessels using catheters or syringes, and can effectively stop blood flow in blood vessels. That is, an application to localized cancer treatment wherein a blood vessel guided to tumorous tissue is closed off to inhibit growth of the tumor is suggested.

EXAMPLE 10

Encapsulation of Substances 50 ml of aqueous chlorophyll solution saturated at standard temperature were added to 1 g of the chitosan derivatives 1-I and 1-a-I prepared according to the present invention. The respective chitosan derivatives immediately absorbed the chlorophyll solution to form a green hydrogel. These gels were not able to be decomposed in 0.1 M acetic acid buffer solution (pH 4.0), 1N hydrochloric acid solution (pH 1) nor 1N sodium hydroxide solution (pH 13).

The above results suggest that the high-water-retention chitosan derivative of the present invention is capable of readily absorbing and encapsulating water-soluble compounds, and can maintain an insoluble gel even under a certain level of non-physiological conditions, so that a wide range of applications in the pharmaceutical and food industries as drug delivery systems or controlled drug release agents can be expected.

EXAMPLE 11

Surface Treatments by Chitosan Derivatives (Functionalization of Solidified Chitosan Derivatives)

(1) Surface Lubrication Treatment by Amphipathic Groups

A 0.1 wt % aqueous solution of the chitosan derivative 1-A1-a with the first and second functionalizations due to the present invention was prepared, and a polyurethane-coated wire (diameter 2 mm, length 5 cm, Kawasuml Laboratories) was immersed in the aqueous solution. Thereafter, it was immediately irradiated with ultraviolet rays for 5 minutes, and rinsed with ethanol and water. The urethane wire treated with 1-A1-a was immersed in a carbonic acid buffer solution (pH 10) containing 5 wt % of lauryl alcohol polyethylene glycol (15) glycydyl ether (EX-171; Nagase Kasei Kogyo), then allowed to react for 20 hours at 80° C. After the reaction, the result was cleansed with ethanol and distilled water to obtain a polyurethane wire (referred to as "1-A1-a-(I)") having a lubrication surface treatment due to the amphipathic groups.

After immersing the resulting surface-treated polyurethane wire 1-A1-a-(I) for 30 seconds in physiological saline solution, 2 cm of the surface-treated portion of the polyurethane wire was gripped through a 1 mm thick silicone sheet by means of a pneumatic clamp adjusted to 2 kg/cm$^2$, then pulled at a rate of 200 mm/minute, measuring the maximum load being applied at the time the polyurethane wire was pulled away from the silicone sheet. This maximum load was used to evaluate the lubricity of the surface. As a control, the same measurements were made on untreated polyurethane wire (N) and a polyurethane wire not treated with EX-171 (treated with 1-A1-a). The results are shown in Table 7.

As shown in Table 7, the surface treated with EX-171, which has an amphipathic group had increased lubricity and was easier to pull away. That is, the functionalized chitosan derivative of the present invention is capable of readily forming a thin film on the surface of a resin due to incorporation of a photo-reactive functional group (second functionalization), and further functionalizations such as, for example, the amphipathic groups can be made after the film has formed. Due to the capability of surface modification wherein further functions such as lubricity and the like can be added after forming the film, the chitosan derivative of the present invention can be used appropriately in the surface treatment of catheters and guide wires as well.

TABLE 7

Maximum Load for Pulling Away Polyurethane Wire

| Surface Treatment | Maximum Pull-away Load (kgf) |
|---|---|
| N (untreated) | 2.00 |
| 1-A1-a | 0.96 |
| 1-A1-a-(I) | 0.18 |

(2) Surface Treatment Due to Glycosaminoglycan (Heparin) (Fourth Functionalization)

The chitosan derivative 1-A1-a of the present invention was dissolved in distilled water, an dimethylsulfoxide was added so as to make the final concentration 1 wt %, to formulate a mixed solution with a chitosan derivative concentration of 1 wt %. The inside of a vinyl chloride tube having an inner diameter of 5 mm and a length of 5 cm was filled with this mixed solution, and after irradiating with ultraviolet rays for 24 hours from outside the tube, the unreacted solution was disposed of and the result was washed with distilled water. In this way, the inner surface of the vinyl chloride tube was coated with a 1-A1-a film.

Separate from the above, low-molecular weight heparin fragments having an aldehyde group incorporated to the reducing terminal by means of a publicly known nitrous acid decomposition method were obtained by gel filtration. An aqueous solution obtained by adding 10 mg of low-molecular weight heparin and 50 mg of cyano sodium boron hydrate to 1 ml of distilled water was prepared, and loaded into the above-mentioned chitosan derivative treated tube which had been washed. After allowing to react for 24 hours at 50° C., the inside of the tube was replaced with 0.01% TWEEN 20 solution, then rinsed with ethanol and distilled water, to obtain a heparinated (fourth functionalization) vinyl chloride tube (1-A1-a-(H)).

Next, a 0.0008% aqueous toluidine blue solution bonding to heparin to form a complex was loaded into the above-described heparinated tube 1-A1-a-(H), and the change in light absorption of the toluidine blue bonded to the heparin was measured at 640 nm. As controls, the same measurements were made using an untreated vinyl chloride tube and a tube which was treated with low-molecular weight heparin without using cyano sodium boron hydrate (i.e. wherein the low-molecular weight heparin does not form covalent bonds, and simply adsorbs to the surface, referred to as "1-A1-a/(H)"). The results are shown in Table 8.

TABLE 8

Change in Light Absorption of Toluidine Blue

| Surface Treatment | Light Absorption |
|---|---|
| None | 0.19 |
| 1-A1-a/(H) | 0.16 |
| 1-A1-a-(H) | 0.06 |

As shown in Table 8, with the functionalized heparin derivative of the present invention incorporating heparin, which is a glycosaminoglycan by means of covalent bonds, the surface treatment by heparin was able to be performed with a higher efficiency than in the case of simple adsorption. Therefore, the chitosan derivative of the present invention is suitable for use in the surface treatment of medical devices such as catheters, guide wires and extracorporeal circulation paths, which contact the blood. Additionally, since the activation of cell growth factors such as FGF due to heparin can be achieved in wound dressings, a wound healing promotion effect can be expected.

In the present example, glycosaminoglycans were incorporated into the surface of the photo-hardened film formed on a resin surface or the like, but as mentioned above, it can also be used after incorporating glycosaminoglycans into the chitosan molecules prior to forming the film.

Industrial Applicability

The functional chitosan derivatives according to the present invention enables solubility at physiological pH levels due to the incorporation of carbohydrates having reducing terminals (first functionalization), is provided with the ability to self-crosslinking by photo-irradiation due to incorporation of photo-reactive functional groups (second functionalization), is able to form an insoluble hydrogel with considerably improved water retention (water absorption) due to incorporation of amphipathic groups (third functionalization), and can promote healing of wounds or work as an anti-thrombotic material due to the incorporation of glycosaminoglycans (fourth functionalization). Accordingly, the functional chitosan derivatives of the present invention can be widely applied to various healthcare materials, for example in the field of medicine, for binding of corporeal tissue, sealing of liquids and gases, prevention of adhesion, against embolisms, as implants, lubricants and for controlled release of pharmaceutical ingredients, and in the field of cosmetics, to skin care and hair protection.

What is claimed is:

1. A functional chitosan derivative comprising an at least partially deacetylated chitin/chitosan attached to at least one photo-reactive functional group selected from the following (A)–(D):

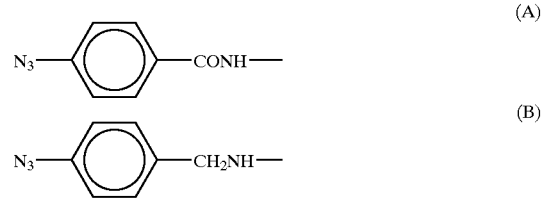

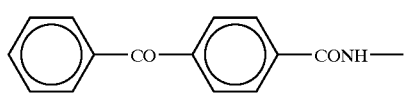

(C)

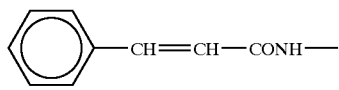

(D)

said functional group(s) being incorporated to an amino group at the 2-position of a glucosamine unit constituting said chitin/chitosan.

2. A health-care material in the form of wound dressings, anti-adhesion materials, hemostatics, sealants for body fluids or gases, clathrates for drug delivery or encapsulating agents for cell adhesives, said health care material comprising a functional chitosan derivative as recited in claim 1.

3. The functional chitosan derivative of claim 1 comprising an additional functional group attached to the at least partially deacetylated chitin/chitosan selected from the group consisting of:

a carbohydrate having a reducing terminal selected from lactose, maltose, melibiose, cellobiose, laminaribiose and mannobiose and equivalents thereof and being incorporated to an amino group at the 2-position of a glucosamine unit constituting said chitin/chitosan;

an amphipathic group being incorporated to an amino group at the 2-position of a glucosamine unit constituting said chitin/chitosan or a hydroxyl group at the 3-position or 6-position of a glucosamine unit or an acetylglucosamine unit constituting said chitin/chitosan;

a glycosaminoglycan being incorporated to an amino group at the 2-position of a glucosamine unit constituting said chitin/chitosan;

and combinations thereof.

* * * * *

UNITED STATES PATENT AND TRADEMARK OFFICE
CERTIFICATE OF CORRECTION

PATENT NO. : 6,806,260 B1
DATED : October 19, 2004
INVENTOR(S) : Yura Hirofumi et al.

It is certified that error appears in the above-identified patent and that said Letters Patent is hereby corrected as shown below:

Column 7,
Line 56, delete "degree of substitutions", and insert -- degree of substitution --.

Column 10,
Line 23, delete "$CH_2-(CH_2)_n-O-(CH_2CH_2O)_m-CH_2-CONH-$ (b)", and insert -- $CH_3-(CH_2)_n-O-(CH_2CH_2O)_m-CH_2-CONH-$ (b) --.

Column 11,
Line 57, delete "issue", and insert -- tissue --.

Column 14,
Line 31, delete "30 degrees", and insert -- 80 degrees --.

Signed and Sealed this

Eighteenth Day of April, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,806,260 B1 | Page 1 of 1 |
| APPLICATION NO. | : 09/831419 | |
| DATED | : October 19, 2004 | |
| INVENTOR(S) | : Yura Hirofumi et al. | |

It is certified that error appears in the above-identified patent and that said Letters Patent is hereby corrected as shown below:

In Column 11:

Please delete the formulas found on lines 1-28, and insert the following therefor:

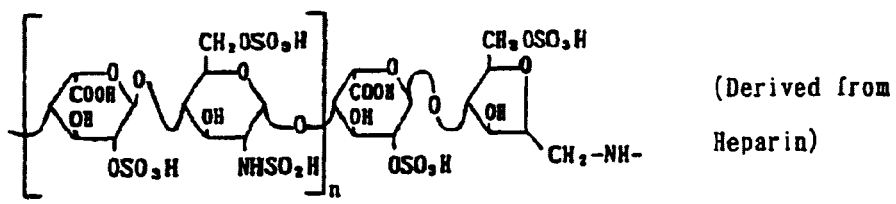

(Derived from Heparin)

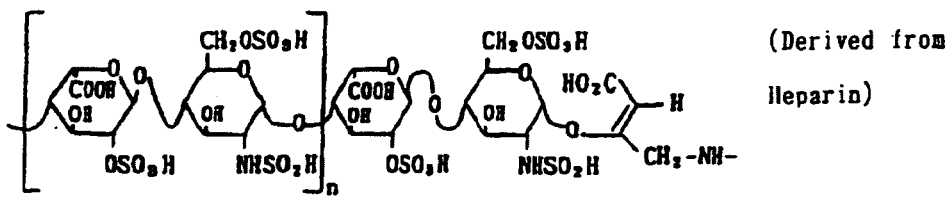

(Derived from Heparin)

Signed and Sealed this

Twenty-sixth Day of September, 2006

JON W. DUDAS
*Director of the United States Patent and Trademark Office*